(12) United States Patent
Knappe et al.

(10) Patent No.: US 10,231,918 B2
(45) Date of Patent: Mar. 19, 2019

(54) AGENT AND METHOD FOR THE TEMPORARY DEFORMATION OF KERATIN-CONTAINING FIBERS

(71) Applicant: Henkel AG & Co. KGaA, Duesseldorf (DE)

(72) Inventors: Thorsten Knappe, Schenefeld (DE); Pamela Kaftan, Hamburg (DE); Maria Catalina Bermudez Agudelo, Hamburg (DE); Tim Bethge, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/363,369

(22) Filed: Nov. 29, 2016

(65) Prior Publication Data

US 2017/0165180 A1    Jun. 15, 2017

(30) Foreign Application Priority Data

Dec. 15, 2015    (DE) .................. 10 2015 225 210

(51) Int. Cl.
| | |
|---|---|
| A61K 8/31 | (2006.01) |
| A61K 8/81 | (2006.01) |
| A61K 8/04 | (2006.01) |
| A61K 8/33 | (2006.01) |
| A61Q 5/06 | (2006.01) |
| B65D 83/14 | (2006.01) |

(52) U.S. Cl.
CPC ............ *A61K 8/8158* (2013.01); *A61K 8/046* (2013.01); *A61K 8/31* (2013.01); *A61K 8/315* (2013.01); *A61K 8/33* (2013.01); *A61K 8/8147* (2013.01); *A61Q 5/06* (2013.01); *B65D 83/752* (2013.01); *A61K 2800/48* (2013.01); *A61K 2800/594* (2013.01); *A61K 2800/87* (2013.01)

(58) Field of Classification Search
CPC .......... A61K 2800/48; A61K 2800/594; A61K 2800/87; A61K 8/046; A61K 8/31; A61K 8/315; A61K 8/33; A61K 8/8147; A61K 8/8158; A61Q 5/06; B65D 83/752
See application file for complete search history.

(56) References Cited

U.S. PATENT DOCUMENTS

| | | | |
|---|---|---|---|
| 5,104,642 A * | 4/1992 | Wells ................ | A61K 8/34 424/47 |
| 6,723,312 B2 | 4/2004 | Dupuis | |
| 2002/0012632 A1 | 1/2002 | Samain et al. | |
| 2007/0197704 A1 | 8/2007 | Walter et al. | |
| 2013/0280178 A1 | 10/2013 | Mueller et al. | |
| 2014/0093469 A1 | 4/2014 | Mueller et al. | |

FOREIGN PATENT DOCUMENTS

| | | |
|---|---|---|
| DE | 102004040172 A1 | 3/2006 |
| EP | 2433614 A2 | 3/2012 |
| GB | 1146155 A | 3/1969 |
| WO | 0113863 A2 | 3/2001 |
| WO | 2005012588 A1 | 2/2005 |

OTHER PUBLICATIONS

English translation of Muller et al. (WO 2012168035); 2012.*
English translation of Bergemann et al. (DE 102004040172); 2006.*
Ultrahold 8 technical data sheet (Sep. 2006; 8 pages).*
Preliminary Amendment for U.S. Appl. No. 15/363,369, dated Nov. 29, 2016.
Substitute Specification for U.S. Appl. No. 15/363,369, dated Nov. 29, 2016.
Intellectual Property Office, Combined Search and Examination Report under Sections 17 and 18(3) for United Kingdom Application No. GB16211385 issued dated 2, 2017.
Intellectual Property Office, Combined Search and Examination Report under Sections 17 and 18(3) for United Kingdom Application No. GB1621170.8 dated Oct. 2, 2017.
National Institute of Industrial Property, Search Report for France Patent Application No. 1662099 dated Dec. 1, 2017.
The Dow Chemical Company, "ACUDYNE Hair Styling Polymers Product Overview," May 2015, pp. 1-4, retrieved from the internet on Feb. 7, 2018 at: http://msdssearch.dow.com/PublishedLiteratureDOWCOM/dh_0933/0901b80380933ea9.pdf?filepath=personalcare/pdfs/noreg/324-00624.pdf&fromPage=GetDoc.
Potzolli et al., "Polymers for hairsprays," Aerosol Spray Report, 1999.

* cited by examiner

*Primary Examiner* — Ernst V Arnold
(74) *Attorney, Agent, or Firm* — Lorenz & Kopf, LLP

(57) ABSTRACT

A cosmetic agent for the temporary deformation of keratinous fibers and a method for the temporary deformation of keratinous fibers using the cosmetic agent are provided. The cosmetic agent comprises:
  a) a cosmetic preparation containing
    a1) at least one copolymer composed at least of the following monomer units:
      styrene
      acrylic acid and/or methacrylic acid;
    a2) at least one copolymer composed at least of the following monomer units:
      N-tert-butylacrylamide
      acrylic acid
      ethyl acrylate,
wherein the weight fraction of copolymers a1) and a2) in the total weight of the cosmetic preparationis about 1.0 to about 10% by weight.

16 Claims, No Drawings

AGENT AND METHOD FOR THE TEMPORARY DEFORMATION OF KERATIN-CONTAINING FIBERS

CROSS-REFERENCE TO RELATED APPLICATION

This application claims priority to German Patent Application No. 10 2015 225 210.8, filed Dec. 15, 2015, which is incorporated herein by reference in its entirety.

TECHNICAL FIELD

The present disclosure relates to a cosmetic composition for setting hair or for temporarily deforming keratinous fibers, in particular human hair, wherein the composition contains a combination of two specific copolymers.

BACKGROUND

The temporary shaping of hairstyles for an extended period of time of up to several days generally requires the use of setting active substances. For this reason, hair treatment agents that are used to temporarily shape the hair play an important role. Corresponding agents for the temporary deformation usually contain synthetic polymers and/or waxes as the setting active substance. Agents for assisting in the temporary deformation of keratin-containing fibers may be provided as hair spray, hair wax, hair gel, or hair foam, for example.

The most important property of an agent for the temporary deformation of hair, also referred to below as a styling agent, is to provide the treated fibers with a preferably strong hold in the reshaped form, i.e., a shape that is imparted to the hair. This is also referred to as a strong hairstyle hold or a high degree of hold of the styling agent. The hairstyle hold is determined essentially by the type and quantity of the setting active substances used, although influence by the other components of the styling agent may also be provided.

Styling agents must meet numerous other requirements besides a high degree of hold. These may be roughly divided into properties on the hair, properties of the particular formulation, such as properties of sprayed aerosols, and properties relating to the use of the styling agent, particular importance being attached to the properties on the hair. Mentioned in particular are moisture resistance, low tack, and a balanced conditioning effect. In addition, a styling agent should preferably be universally usable for all types of hair and be mild on the hair and skin.

In order to meet the various requirements, a number of synthetic polymers used in styling agents have already been developed as setting active substances. These polymers may be divided into cationic, anionic, nonionic, and amphoteric setting polymers.

Hair-setting agents based on copolymers of styrene with (meth)acrylic acid and/or the esters thereof are described in International Patent application WO 2012/168035 A1.

Hair sprays based on copolymers of N-tert-butylacrylamide, acrylic acid, and ethyl acrylate are described in German Patent application DE 10 2004 040 172 A1, among other publications.

Not every polymer, and not every polymer mixture, is basically suited for producing hair styling agents. This is particularly true for hair sprays, in which, for example, the viscosity and thus also the spray characteristics are influenced by the polymer and the quantity of polymer used.

Although suitable polymers and polymer combinations have been developed some time ago for use in the area of temporary hair deformation, the results achieved thus far still leave room for improvements, in particular with regard to the storage stability, the applicability, and the degree of hold of these agents. In particular, currently available styling agents are in need of further improvement, since a good combination of the degree of hold and the long-term hold (high humidity curl retention) is not always sufficiently ensured.

BRIEF SUMMARY

Cosmetic agents for the temporary deformation of keratinous fibers, cosmetic products, and methods for the temporary deformation of keratin-containing fibers using the cosmetic agents are provided. In accordance with an exemplary embodiment, a cosmetic agent for the temporary deformation of keratinous fibers is provided. The cosmetic agent comprises:
  a) a cosmetic preparation comprising:
    a1) at least one copolymer composed at least of the following monomer units:
      styrene
      acrylic acid and/or methacrylic acid; and
    a2) at least one copolymer composed at least of the following monomer units:
      N-tert-butylacrylamide
      acrylic acid
      ethyl acrylate,
wherein the weight fraction of copolymers a1) and a2) in the total weight of the cosmetic preparation is about 1.0 to about 10% by weight.

In accordance with another exemplary embodiment, a cosmetic product is provided. The cosmetic product comprises:
  i) a cosmetic agent comprising:
    a) a cosmetic preparation comprising:
      a1) at least one copolymer composed at least of the following monomer units:
        styrene
        acrylic acid and/or methacrylic acid; and
      a2) at least one copolymer composed at least of the following monomer units:
        N-tert-butylacrylamide
        acrylic acid
        ethyl acrylate,
wherein the weight fraction of copolymers a1) and a2) in the total weight of the cosmetic preparation is about 1.0 to about 10% by weight; and
  ii) a dispensing device having a spray valve.

In accordance with a further embodiment, a method for the temporary deformation of keratin-containing fibers, in particular human hair, in which the keratinous fibers are acted on by a cosmetic agent and temporarily fixed in shape is provided. The cosmetic agent comprises:
  a) a cosmetic preparation comprising:
    a1) at least one copolymer composed at least of the following monomer units:
      styrene
      acrylic acid and/or methacrylic acid; and
    a2) at least one copolymer composed at least of the following monomer units:
      N-tert-butylacrylamide
      acrylic acid
      ethyl acrylate, wherein the weight fraction of copolymers a1) and a2) in the total weight of the cosmetic preparation is about 1.0 to about 10% by weight.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Cosmetic agents contemplated herein provide suitable polymer combinations which are characterized by good film-forming and/or setting properties and which have a very high degree of hold, without having to forgo flexibility and good moisture resistance, in particular to perspiration, and water resistance. The polymer combinations are suitable for producing cosmetic compositions having high chemical and physical stability, and are easy to apply.

The cosmetic agents contemplated herein provide a combination of two specific, different copolymers. In particular, the cosmetic agents contemplated herein provide the following:

1. A cosmetic agent for the temporary deformation of keratinous fibers, comprising
   a) a cosmetic preparation containing
      a1) at least one copolymer composed at least of the following monomer units:
         styrene
         acrylic acid and/or methacrylic acid;
      a2) at least one copolymer composed at least of the following monomer units:
         N-tert-butylacrylamide
         acrylic acid
         ethyl acrylate,
   wherein the weight fraction of copolymers a1) and a2) in the total weight of the cosmetic preparation is about 1.0 to about 10% by weight.
2. The cosmetic agent according to item 1, wherein the weight fraction of copolymers a1) and a2) in the total weight of the cosmetic preparation is about 1.5 to about 9.0% by weight and in particular about 2.0 to about 8.0% by weight, respectively.
3. The cosmetic agent according to one of the preceding items, wherein the at least one copolymer a1), based on its total weight, is composed of at least about 90% by weight, preferably at least about 95% by weight, and in particular at least about 97% by weight of the monomers
   styrene
   acrylic acid and/or methacrylic acid.
4. The cosmetic agent according to one of the preceding items, wherein the at least one copolymer a1), based on its total weight, is composed of at least about 90% by weight, preferably at least about 95% by weight, and in particular at least about 97% by weight of the monomers
   styrene
   acrylic acid and/or methacrylic acid
   acrylic acid ester and/or methacrylic acid ester.
5. The cosmetic agent according to one of the preceding items, wherein copolymer a1) has the INCI name Styrene/Acrylates Copolymer.
6. The cosmetic agent according to one of the preceding items, wherein the preparation, based on its total weight, contains about 0.1 to about 9.9% by weight, preferably about 0.5 to about 8.5% by weight, and in particular about 1.0 to about 7.0% by weight of copolymer a1).
7. The cosmetic agent according to one of the preceding items, wherein the at least one copolymer a2), based on its total weight, is composed of at least about 90% by weight, preferably at least about 95% by weight, and in particular at least about 97% by weight of the monomers
   N-tert-butylacrylamide
   acrylic acid
   ethyl acrylate.
8. The cosmetic agent according to one of the preceding items, wherein copolymer a2) has the INCI name Acrylates/t-Butylacrylamide Copolymer.
9. The cosmetic agent according to one of the preceding items, wherein the preparation, based on its total weight, contains about 0.1 to about 9.9% by weight, preferably about 0.5 to about 8.5% by weight, and in particular about 1.0 to about 7.0% by weight of copolymer a2).
10. The cosmetic agent according to one of the preceding items, wherein the weight ratio of copolymer a1) to copolymer a2) is about 1:7 to about 7:1, preferably about 1:5 to about 5:1, and in particular about 1:3 to about 3:1.
11. The cosmetic agent according to one of the preceding items, wherein the preparation, based on its total weight, contains about 40 to about 98% by weight, preferably about 60 to about 95% by weight, and in particular about 70 to about 92% by weight of polar solvent.
12. The cosmetic agent according to one of the preceding items, wherein the preparation, based on its total weight, is composed of at least about 70% by weight, preferably at least about 80% by weight, and in particular at least about 90% by weight of copolymers a1) and a2), ethanol, and/or water.
13. The cosmetic agent according to one of the preceding items, wherein the cosmetic preparation also includes at least one thickener, preferably from the group of polymeric organic thickeners.
14. The cosmetic agent according to one of the preceding items, wherein the cosmetic preparation also includes at least one thickener from the group of anionic polymeric organic thickeners.
15. The cosmetic agent according to one of the preceding items, wherein the cosmetic preparation also includes at least one thickener from the group of anionic, polymeric, amphiphilic thickeners.
16. The cosmetic agent according to one of the preceding items, wherein the cosmetic preparation also includes at least one thickener from the group with the INCI names Acrylates/Beheneth-25 Methacrylate Copolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-20 Acrylate Copolymer, Acrylates/Palmeth-25 Acrylate Copolymer, Acrylates/Palmeth-25 Itaconate Copolymer, and Acrylates/Steareth-50 Acrylate Copolymer.
17. The cosmetic agent according to one of the preceding items, wherein the preparation, based on its total weight, contains about 0.05 to about 8.0% by weight, preferably about 0.1 to about 5.0% by weight, of thickener.
18. The cosmetic agent according to one of the preceding items, wherein the agent also includes
    b) at least one propellant.
19. The cosmetic agent according to one of the preceding items, wherein the agent also includes
    b) at least one propellant from the group propane, a mixture of propane and butane, dimethyl ether, and 1,1-difluoroethane.

20. The cosmetic agent according to one of the preceding items which, based on its total weight, includes
    a) about 30 to about 70% by weight of the cosmetic preparation
    b) about 30 to about 70% by weight of propellant.
21. A cosmetic product comprising
    i) a cosmetic agent according to one of items 1 to 20
    ii) a dispensing device having a spray valve.
22. Use of an agent or a product according to one of items 1 to 21 for the temporary deformation of keratin-containing fibers, in particular human hair.
23. A method for the temporary deformation of keratin-containing fibers, in particular human hair, in which the keratinous fibers are acted on by a cosmetic agent according to one of items 1 to 21 and temporarily fixed in shape.

It has surprisingly been found as contemplated herein that improved moisture resistance of styling products may be obtained by combining two components, known per se, already used in styling products. Other properties of styling products which are customarily required, such as long-term hold, stiffness, and low tack, are maintained or improved. Such a good combination of properties was not to be expected, even with knowledge of the individual components, and was surprising. It has been shown experimentally that a highly superadditive, i.e., synergistic, effect with regard to moisture resistance and the degree of hold has been obtained by the combination of the two components.

As contemplated herein, the term "keratinous fibers" includes fur, wool, and feathers, but in particular human hair.

The essential components of the cosmetic composition contemplated herein are the anionic copolymer a1) and the anionic copolymer a2), which is different from copolymer a1).

The cosmetic preparations as contemplated herein contain an anionic copolymer a1) as the first essential component.

With regard to the manufacturability, applicability, and cosmetic effect of cosmetic agents contemplated herein, it has proven advantageous when the weight fraction of copolymer a1) in the total weight of cosmetic preparation a) is about 0.1 to about 9.9% by weight, preferably about 0.5 to about 8.5% by weight, and in particular about 1.0 to about 7.0% by weight.

Copolymer a1) may be based on the monomers i) styrene and ii) acrylic acid and/or methacrylic acid, and optionally further monomers.

Preferred copolymers a1) are preferably composed of at least about 90% by weight, preferably at least about 95% by weight, and in particular at least about 97% by weight of the monomers styrene and acrylic acid and/or methacrylic acid. Particularly preferred copolymers a1) have been obtained solely from the monomers styrene and acrylic acid and/or methacrylic acid.

The cosmetic agents in another preferred embodiment are characterized in that the at least one copolymer a1), based on its total weight, is composed of at least about 90% by weight, preferably at least about 95% by weight, and in particular at least about 97% by weight of the monomers
    styrene
    acrylic acid and/or methacrylic acid
    acrylic acid ester and/or methacrylic acid ester.

The above-described copolymers a1) are marketed, for example, by Dow Chemicals under the name Acudyne® Shine (INCI name: Styrene/Acrylates Copolymer; CAS No. 9010-92-8).

Copolymer a1) is preferably used in the cosmetic preparation in partially neutralized or neutralized form. At least one alkanolamine is preferably used for the neutralization. The alkanolamines which are usable as alkalizing agent as contemplated herein are preferably selected from primary amines having a $C_2$-$C_6$ alkyl base structure bearing at least one hydroxyl group. Particularly preferred alkanolamines are selected from the group comprising 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, and 2-amino-2-methylpropane-1,3-diol. Alkanolamines very particularly preferred as contemplated herein are selected from the group 2-aminoethan-1-ol, 2-amino-2-methylpropan-1-ol, and 2-amino-2-methylpropane-1,3-diol. 2-Amino-2-methylpropanol has proven to be a particularly suitable neutralizing agent. Cosmetic agents preferred as contemplated herein contain at least one alkanolamine, preferably 2-amino-2-methylpropanol. The 2-amino-2-methylpropanol is preferably used in the cosmetic preparations as contemplated herein in a quantity which does not exceed the quantity necessary for neutralizing the copolymer a1). The quantities of 2-amino-2-methylpropanol used in the cosmetic preparations contemplated herein are preferably about 80 to about 100%, particularly preferably about 90 to about 100%, and in particular about 95 to about 100% of the quantity necessary for completely neutralizing the copolymer a1). In one preferred embodiment, the weight fraction of 2-amino-2-methylpropanol in the total weight of cosmetic preparation a) is about 0.1 to about 4.0% by weight, preferably about 0.5 to about 3.0% by weight, and in particular about 1.0 to about 2.0% by weight.

The cosmetic preparations contemplated herein contain an anionic acrylate copolymer a2) as the second essential component.

With regard to the manufacturability, applicability, and cosmetic effect of cosmetic agents contemplated herein, it has proven advantageous when the weight fraction of copolymer a2) in the total weight of cosmetic preparation a) is about 0.1 to about 9.9% by weight, preferably about 0.5 to about 8.5% by weight, and in particular about 1.0 to about 7.0% by weight.

Copolymer a2) may be based on the monomers N-tert-butylacrylamide, acrylic acid, ethyl acrylate, and optionally further monomers.

Preferred copolymers a2) are preferably composed of at least about 90% by weight, preferably at least about 95% by weight, and in particular at least about 97% by weight of the monomers i) N-tert-butylacrylamide, ii) acrylic acid, iii) ethyl acrylate. Particularly preferred copolymers a2) have been obtained solely from the monomers i) N-tert-butylacrylamide, ii) acrylic acid, and iii) ethyl acrylate.

The above-described copolymers a2) are marketed, for example, by BASF under the name Ultrahold® 8 (INCI name: Acrylates/t-Butylacrylamide Copolymer; CAS No. 26062-56-6).

Copolymer a2) is preferably used in the cosmetic agents in partially neutralized or neutralized form. At least one alkanolamine is preferably used for the neutralization. The alkanolamines which are usable as alkalizing agent as contemplated herein are preferably selected from primary amines having a $C_2$-$C_6$ alkyl base structure bearing at least one hydroxyl group. Particularly preferred alkanolamines are selected from the group comprising 2-aminoethan-1-ol (monoethanolamine), tris(2-hydroxyethyl)amine (triethanolamine), 3-aminopropan-1-ol, 4-aminobutan-1-ol, 5-aminopentan-1-ol, 1-aminopropan-2-ol, 1-aminobutan-2- ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2- and amino-2-methylpropane-1,3-diol. Alkanolamines very particularly preferred as contemplated herein are selected from the group 2-aminoethan-1-ol, 2-amino-2-methylpropan-1-ol, and 2-amino-2-methylpropane-1,3-diol. 2-Amino-2-methylpropanol has proven to be a particularly suitable neutralizing agent. Cosmetic agents preferred as contemplated herein contain at least one alkanolamine, preferably 2-amino-2-methylpropanol. The 2-amino-2-methylpropanol is preferably used in the cosmetic agents contemplated herein in a quantity which does not exceed the quantity necessary for neutralizing the copolymer a2). The quantities of 2-amino-2-methylpropanol used in the cosmetic preparations contemplated herein are preferably about 80 to 100%, particularly preferably about 90 to 100%, and in particular about 95 to 100% of the quantity necessary for completely neutralizing the copolymer a2). In one preferred embodiment, the weight fraction of 2-amino-2-methylpropanol in the total weight of the cosmetic preparation a) is about 0.1 to about 4.0% by weight, preferably about 0.5 to about 3.0% by weight, and in particular about 1.0 to about 2.0% by weight.

The weight fraction of copolymers a1) and a2) in the total weight of the cosmetic preparation is about 1.0 to about 10% by weight. Cosmetic preparations are preferred in which the weight fraction of copolymers a1) and a2') in the total weight of the cosmetic preparation is about 1.5 to about 9.0% by weight, in particular about 2.0 to about 8.0% by weight.

In addition to the total weight fraction of copolymers a1) and a2), the weight ratio of copolymers a1) and a2) with respect to one another also has an influence on the moisture resistance, the degree of hold, and the other application properties of cosmetic agents contemplated herein. Cosmetic agents that are particularly advantageous technically are characterized in that the weight ratio of copolymer a1) to copolymer a2) is about 1:7 to about 7:1, preferably about 1:5 to about 5:1, and in particular about 1:3 to about 3:1.

In addition to the above-described copolymers a1) and copolymers a2), the cosmetic preparations contemplated herein may contain further active substances, auxiliary substances, and care substances.

Film-forming polymers constitute a first group of preferably used active substances. These film-forming polymers are not identical to copolymer a1) or copolymer a2) described above. The weight fraction of the film-forming polymer in the total weight of the cosmetic preparation is preferably about 0.1 to about 8.0% by weight, preferably about 0.5 to about 6.0% by weight, and in particular about 1.0 to about 4.0% by weight.

Nonionic polymers are particularly preferably used as film-forming polymers. Examples of suitable nonionic polymers include the following:
  vinylpyrrolidone/vinyl ester copolymers as marketed, for example, under the trade name Luviskol® (BASF). Luviskol® VA 64 and Luviskol® VA 73, each of which are vinylpyrrolidone/vinyl acetate copolymers, are preferred nonionic polymers.
  cellulose ethers such as hydroxypropylcellulose, hydroxyethylcellulose, and methylhydroxypropylcellulose as marketed, for example, under the trade names Culminal® and Benecel® (Aqualon).
  shellac.
  polyvinylpyrrolidones as marketed, for example, under the name Luviskol® (BASF).
  siloxanes. These siloxanes may be water-soluble as well as nonwater-soluble. Volatile as well as nonvolatile siloxanes are suitable; nonvolatile siloxanes are understood to mean those compounds whose boiling point at standard pressure is above 200° C. Preferred siloxanes are polydialkylsiloxanes, for example polydimethylsiloxane, polyalkylarylsiloxanes, for example polyphenylmethylsiloxane, ethoxylated polydialkylsiloxanes, and polydialkylsiloxanes which contain amine and/or hydroxy groups.
  glycosidically substituted silicones.

Due to their cosmetic effect in combination with copolymers a1) and a2), film-forming polymers preferably used as contemplated herein are in particular polyvinylpyrrolidones (INCI name: PVP) and vinylpyrrolidone/vinyl acetate copolymers (INCI name: VP/VA Copolymer), wherein the weight fraction of these polymers is preferably limited to quantities between about 1.0 and about 10% by weight. Particularly preferred cosmetic preparations contemplated herein are therefore characterized in that, based on their total weight, they also contain about 1.0 to about 10% by weight polyvinylpyrrolidone and/or vinylpyrrolidone/vinyl acetate copolymer, preferably polyvinylpyrrolidone. Particularly preferred cosmetic preparations have a weight fraction of polyvinylpyrrolidone and/or vinylpyrrolidone/vinyl acetate copolymer in the total weight of the cosmetic preparation of about 2.0 to about 8.5% by weight, preferably about 3.0 to about 7.0% by weight.

In summary, cosmetic agents particularly preferred as contemplated herein, including copolymers a1) and a2) and the film-forming polymer a3), contain three different polymers.

Protein hydrolysates and/or the derivatives thereof may be used as care substance. Protein hydrolysates are product mixtures that are obtained by acidically, basically, or enzymatically catalyzed degradation of proteins. As contemplated herein, the term "protein hydrolysates" is also understood to mean total hydrolysates and individual amino acids and the derivatives thereof, as well as mixtures of various amino acids. The molar weight of the protein hydrolysates that are usable herein is between about 75 (the molar weight of glycine) and about 200,000 Dalton; the molar weight is preferably about 75 to about 50,000 Dalton, and very particularly about 75 to about 20,000 Dalton.

Vitamins, provitamins, vitamin precursors, and/or the derivatives thereof constitute another group of care substances. As contemplated herein, vitamins, provitamins and vitamin precursors generally associated with the groups A, B, C, E, F, and H are preferred.

Further care substances are glycerin, propylene glycol, panthenol, caffeine, nicotinamide, and sorbitol.

Plant extract and also mono- and oligosaccharides and/or lipids may be used as care substance.

The compositions of several cosmetic preparations a), in which the weight fraction of copolymers a1) and a2) in the total weight of the cosmetic preparation is about 1.0 to about 10% by weight, preferably about 1.5 to about 9.0% by weight, and in particular about 2.0 to about 8.0% by weight, may be found in the following tables. (Unless stated otherwise, the indications in % by weight refer to the total weight of the cosmetic agent.)

|  | Formula 1 | Formula 2 | Formula 3 | Formula 4 | Formula 5 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Optional additives | to make 100 | to make 100 | to make 100 | to make 100 | to make 100 |

|  | Formula 6 | Formula 7 | Formula 8 | Formula 9 | Formula 10 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Optional additives | to make 100 | to make 100 | to make 100 | to make 100 | to make 100 |

|  | Formula 11 | Formula 12 | Formula 13 | Formula 14 | Formula 15 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Optional additives | to make 100 | to make 100 | to make 100 | to make 100 | to make 100 |

|  | Formula 16 | Formula 17 | Formula 18 | Formula 19 | Formula 20 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Optional additives | to make 100 | to make 100 | to make 100 | to make 100 | to make 100 |

* according to Claim 1

The cosmetic preparations contemplated herein may be provided in different ways. The weight fraction and the exact composition of the liquid carrier optionally contained in the cosmetic preparation have a significant influence on the ultimate provided form of these preparations.

Preferred cosmetic agents are based on an aqueous, aqueous/alcoholic, or alcoholic carrier. Thus, preferred cosmetic agents, based on their total weight, contain about 40 to about 98% by weight, preferably about 60 to about 95% by weight, and in particular about 70 to about 92% by weight of polar solvent, preferably polar solvent from the group water, ethanol, and isopropanol.

As previously mentioned, the lower alcohols having 1 to 4 carbon atoms, for example ethanol and isopropanol, customarily used for cosmetic purposes may be contained as alcohols.

In addition to these alcoholic solvents, water-soluble cosolvents, in particular in combination with water, are also usable. Examples of particularly preferred cosolvents are glycerin and/or ethylene glycol and/or 1,2-propylene glycol, which are preferably used in a quantity of 0 to about 30% by weight, based on cosmetic preparation a).

Together with copolymers a1) and a2) described above, the aqueous, aqueous/alcoholic, or alcoholic carriers preferably form an essential component of cosmetic preparations a) contemplated herein. Particularly preferred are cosmetic preparations which, based on their total weight, are composed of at least about 70% by weight, preferably at least about 80% by weight, and in particular at least about 90% by weight of copolymers a1) and a2), ethanol, and/or water.

The composition of several technically advantageous cosmetic preparations a) having a liquid carrier, in which the weight fraction of copolymers a1) and a2) in the total weight of the cosmetic preparation is about 1.0 to about 10% by weight, preferably about 1.5 to about 9.0% by weight, and in particular about 2.0 to about 8.0% by weight, may be found in the following tables. (Unless stated otherwise, the indications in % by weight refer to the total weight of the cosmetic agent.)

|  | Formula 21 | Formula 22 | Formula 23 | Formula 24 | Formula 25 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

|  | Formula 26 | Formula 27 | Formula 28 | Formula 29 | Formula 30 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

|  | Formula 31 | Formula 32 | Formula 33 | Formula 34 | Formula 35 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

-continued

|  | Formula 36 | Formula 37 | Formula 38 | Formula 39 | Formula 40 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

\* according to Claim 1

Of course, it is possible not only to vary the weight fraction of the liquid carrier in the total weight of the cosmetic preparation a), but also to change the weight ratio of aqueous to alcoholic carrier.

The composition of several technically advantageous cosmetic preparations a) having a liquid carrier, in which the weight fraction of copolymers a1) and a2) in the total weight of the cosmetic preparation is about 1.0 to about 10% by weight, preferably about 1.5 to about 9.0% by weight, and in particular about 2.0 to about 8.0% by weight, may be found in the following tables. (Unless stated otherwise, the indications in % by weight refer to the total weight of the cosmetic agent.) Corresponding cosmetic preparations are suitable as pump sprays, for example.

Cosmetic Preparations a) Having a High Ethanol Content

|  | Formula 41 | Formula 42 | Formula 43 | Formula 44 | Formula 45 |
|---|---|---|---|---|---|
| Copolymer a1) \* | 0.1 to 9.9 | 0.1 to 8.9 | 0.5 to 8.0 | 0.5 to 7.5 | 1.0 to 7.0 |
| Copolymer a2) \* | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | to make 100 | to make 100 | to make 100 | to make 100 | to make 100 |

|  | Formula 46 | Formula 47 | Formula 48 | Formula 49 | Formula 50 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Copolymer a2) \* | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | to make 100 | to make 100 | to make 100 | to make 100 | to make 100 |

|  | Formula 51 | Formula 52 | Formula 53 | Formula 54 | Formula 55 |
|---|---|---|---|---|---|
| Copolymer a1) \* | 0.1 to 9.9 | 0.1 to 8.9 | 0.5 to 8.0 | 0.5 to 7.5 | 1.0 to 7.0 |
| Acrylates/t-butylacrylamide Copolymer (INCI) | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | to make 100 | to make 100 | to make 100 | to make 100 | to make 100 |

|  | Formula 56 | Formula 57 | Formula 58 | Formula 59 | Formula 60 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | to make 100 | to make 100 | to make 100 | to make 100 | to make 100 |

\* according to Claim 1

Cosmetic Preparations a) Having an Average Ethanol Content

|  | Formula 61 | Formula 62 | Formula 63 | Formula 64 | Formula 65 |
|---|---|---|---|---|---|
| Copolymer a1) \* | 0.1 to 9.9 | 0.1 to 8.9 | 0.5 to 8.0 | 0.5 to 7.5 | 1.0 to 7.0 |
| Copolymer a2) \* | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | to make 100 | to make 100 | to make 100 | to make 100 | to make 100 |

|  | Formula 66 | Formula 67 | Formula 68 | Formula 69 | Formula 70 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |

-continued

|  | | | | | |
|---|---|---|---|---|---|
| Copolymer a2) * | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | to make 100 | to make 100 | to make 100 | to make 100 | to make 100 |

|  | Formula 71 | Formula 72 | Formula 73 | Formula 74 | Formula 75 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | to make 100 | to make 100 | to make 100 | to make 100 | to make 100 |

|  | Formula 76 | Formula 77 | Formula 78 | Formula 79 | Formula 80 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | to make 100 | to make 100 | to make 100 | to make 100 | to make 100 |

* according to Claim 1

Cosmetic Preparations a) Having a Low Ethanol Content

|  | Formula 81 | Formula 82 | Formula 83 | Formula 84 | Formula 85 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | to make 100 | to make 100 | to make 100 | to make 100 | to make 100 |

|  | Formula 86 | Formula 87 | Formula 88 | Formula 89 | Formula 90 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | to make 100 | to make 100 | to make 100 | to make 100 | to make 100 |

|  | Formula 91 | Formula 92 | Formula 93 | Formula 94 | Formula 95 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | to make 100 | to make 100 | to make 100 | to make 100 | to make 100 |

|  | Formula 96 | Formula 97 | Formula 98 | Formula 99 | Formula 100 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | to make 100 | to make 100 | to make 100 | to make 100 | to make 100 |

* according to Claim 1

Conceivable packaging forms for cosmetic preparations a) as contemplated herein are creams and lotions as well as gels. However, these preparations are also suitable for use as a mousse, foam, or spray.

Gel-form cosmetic preparations contain at least one thickener as a further component. With regard to the manufacturability, applicability, and cosmetic effect of cosmetic compositions contemplated herein, it has proven advantageous when the weight fraction of the thickener in the total weight of the cosmetic preparation a) is about 0.05 to about 8.0% by weight, preferably about 0.1 to about 5.0% by weight.

Preferred thickeners are selected from the group of polymeric organic thickeners. The polymeric organic thickeners may be crosslinked or uncrosslinked.

Preferred thickeners are selected from the group of anionic, polymeric organic thickeners. A first group of particularly preferred thickeners contains at least one structural unit selected from at least one structural unit of formula (I) or the salt forms thereof, or at least one structural unit (II) or the salt forms thereof:

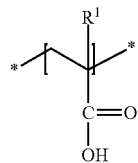
(I)

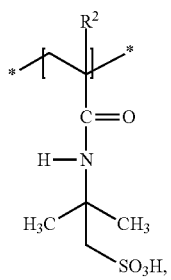
(II)

where $R^1$ and $R^2$ independently stand for a hydrogen atom or a methyl group.

According to the above formulas and all of the following formulas, a chemical bond, denoted by the symbol "*," stands for a free valence of the corresponding structural fragment.

Particularly preferred anionic polymers having a thickening effect contain at least one structural unit of formula (I). Acrylic acid homopolymers form a first group of particularly preferred thickeners.

Particularly preferred thickeners are polyacrylic acids with the INCI name Carbomer, as marketed, for example, by 3V Sigma under the trade name Synthalen® K, or by Lubrizol under the trade name Carbopol.

The anionic, polymeric, amphiphilic thickeners form a second particularly preferred group of thickeners. Corresponding thickeners preferably include at least one structural unit of formula (III) and at least one structural unit of formula (IV):

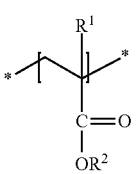
(III)

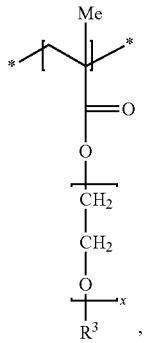
(IV)

where
$R^1$ stands for a hydrogen atom or a methyl group,
$R^2$ stands for a hydrogen atom or a ($C_1$ to $C_6$) alkyl group,
$R^3$ stands for a ($C_8$ to $C_{30}$) alkyl group,
$M^+$ stands for a physiologically acceptable cation, and
x stands for an integer from 0 to 35.

Particularly preferred are the thickeners with the INCI names Acrylates/Beheneth-25 Methacrylate Copolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-20 Acrylate Copolymer, Acrylates/Palmeth-25 Acrylate Copolymer, Acrylates/Palmeth-25 Itaconate Copolymer, and Acrylates/Steareth-50 Acrylate Copolymer.

Particularly preferred thickeners are
thickeners with the INCI name Acrylates/Steareth-20 Methacrylate Copolymer as marketed, for example, by Rohm and Haas under the trade name Aculyn® 22;
thickeners with the INCI name Acrylates/Steareth-20 Methacrylate Crosspolymer as marketed, for example, by Rohm and Haas under the trade name Aculyn® 88;
thickeners with the INCI name Acrylates/Steareth-20 Itaconate Copolymer as marketed, for example, by National Starch under the trade name Structure 2001.

Further anionic, polymeric, amphiphilic thickeners are characterized by long-chain alkyl substituents. This group includes, for example, the compounds with the INCI names Acrylates/Stearyl Methacrylate Copolymer and Acrylates/Vinyl Isodecanoate Crosspolymer.

Particularly preferred thickeners are
thickeners with the INCI name Acrylates/$C_{10-30}$ Alkyl Acrylate Crosspolymer as marketed, for example, by Lubrizol under the trade name Carbopol Ultrez 21.

Further thickeners may be selected, for example, from among the polymeric thickening agents known under the following INCI names: Acrylamides Copolymer, Acrylamide/Sodium Acrylate Copolymer, Acrylamide/Sodium Acryloyldimethyl Taurate Copolymer, Acrylates/Acetoacetoxyethyl Methacrylate Copolymer, Acrylic Acid/Acrylonitrogens Copolymer, Agar, Agarose, *Alcaligenes* Polysaccharides, Algin, Alginic Acid, Ammonium Acrylates/Acrylonitrogens Copolymer, Ammonium Acrylates Copolymer, Ammonium Acryloyldimethyl Taurate/Vinyl Formamide Copolymer, Ammonium Acryloyldimethyl Taurate/VP Copolymer, Ammonium Alginate, Ammonium Polyacryloyldimethyl Taurate, Amylopectin, Ascorbyl Methylsilanol Pectinate, *Astragalus* Gummifer Gum, Attapulgite, *Avena Sativa* (Oat) Kernel Flour, Bentonite, Butoxy Chitosan, *Caesalpinia Spinosa* Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, *Ceratonia Siliqua* Gum, Cetyl Hydroxyethylcellulose, Cholesterol/HDI/Pullulan Copolymer, Cholesteryl Hexyl Dicarbamate Pullulan, *Cyamopsis Tetragonoloba* (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, *Glycine Soja* (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, *Sclerotium* Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, *Solanum Tuberosum* (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia *Urens* Gum, Synthetic Fluorphlogopite, Tamarindus Indica Seed Gum, Tapioca Starch, TEA-Alginate, TEA-Carbomer, *Triticum Vulgare* (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, *Zea Mays* (Corn) Starch.

The composition of several technically advantageous cosmetic preparations a) having a liquid carrier, in which the weight fraction of copolymers a1) and a2) in the total weight of the cosmetic preparation is about 1.0 to about 10% by weight, preferably about 1.5 to about 9.0% by weight, and in particular about 2.0 to about 8.0% by weight, may be found in the following tables. (Unless stated otherwise, the indications in % by weight refer to the total weight of the cosmetic agent.)

|  | Formula 101 | Formula 102 | Formula 103 | Formula 104 | Formula 105 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

|  | Formula 106 | Formula 107 | Formula 108 | Formula 109 | Formula 110 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

|  | Formula 111 | Formula 112 | Formula 113 | Formula 114 | Formula 115 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |

-continued

| | | | | | |
|---|---|---|---|---|---|
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

| | Formula 116 | Formula 117 | Formula 118 | Formula 119 | Formula 120 |
|---|---|---|---|---|---|
| Styrene/Acrylates Copolymer (INCI) | 0.1 to 9.9 | 0.1 to 8.9 | 0.5 to 8.0 | 0.5 to 7.5 | 1.0 to 7.0 |
| Acrylates/t-Butylacrylamide Copolymer (INCI) | 0.1 to 9.9 | 0.1 to 8.9 | 0.5 to 8.0 | 0.5 to 7.5 | 1.0 to 7.0 |
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | to make 100 | to make 100 | to make 100 | to make 100 | to make 100 |

* according to Claim 1

Mousse, foam, or spray may be provided without addition of a propellant, for example by means of a mechanical pumping, foaming, or spraying device, or also using a propellant (aerosol spray, for example). Corresponding cosmetic agents then also include at least one propellant b) in addition to the cosmetic preparation a).

Suitable propellants (propellant gases) are propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, individually and also in combination. Hydrophilic propellant gases such as carbon dioxide may also be advantageously used as contemplated herein when the proportion of hydrophilic gases is selected to be low, and lipophilic propellant gas (propane/butane, for example) is present in excess. Propane, n-butane, isobutane, and mixtures of these propellant gases are particularly preferred. Preferred cosmetic agents are characterized in that the agent also includes at least one propellant b) from the group propane, a mixture of propane and butane, dimethyl ether, and 1,1-difluoroethane (INCI: Hydrofluorocarbon 152a).

The further composition of several preferred cosmetic agents which in addition to cosmetic preparation a) also include a propellant b), and in which the weight fraction of copolymers a1) and a2) in the total weight of the cosmetic preparation is about 1.0 to about 10% by weight, preferably about 1.5 to about 9.0% by weight, and in particular about 2.0 to about 8.0% by weight, may be found in Tables 1 and 2 below.

Several preferred cosmetic agents having a content of cosmetic preparation a) and propellant b) are described in Tables 1 and 2 below.

Table 1 shows cosmetic agents having a low propellant content (mousses, for example), and Table 2 shows cosmetic agents having a high propellant content (sprays, for example).

In Tables 1 and 2, the left column ("Formula x") refers in each case to one of the cosmetic preparations a) of formulas 1 to 100 by way of example, listed in the tables presented above. Columns two through five ("propellant") in each case indicate the quantity of propellant that is combined with the corresponding cosmetic preparation. These indications in "% by weight" refer to the total weight of cosmetic preparation a) having the particular "Formula x," without propellant.

The indication "4 to 12.5% by weight" in Table 1 below thus corresponds to the addition of propellant to cosmetic preparation a) in a quantity that is about 4 to about 12.5% by weight of the weight of cosmetic preparation a). In other words, the cosmetic preparation a) and the propellant b) are present in this cosmetic agent in a weight ratio of about 100:4 to about 100:12.5 and about 25:1 to about 8:1, respectively.

In other words, the cosmetic agents according to line 2, column 4 in Table 1 below are mixtures of the propellant-free cosmetic preparation a) according to formula 1 in the above table with propane/butane in a weight ratio of about 100:4 to about 100:12.5 or, stated another way, are cosmetic agents for the temporary deformation of keratinous fibers, comprising
   a) a cosmetic preparation containing
      a1) about 0.1 to about 9.9% by weight of at least one copolymer composed at least of the following monomer units:
      styrene
      acrylic acid and/or methacrylic acid;
      a2) about 0.1 to about 9.9% by weight of at least one copolymer composed at least of the following monomer units:
      N-tert-butylacrylamide
      acrylic acid
      ethyl acrylate,
   b) propellant from the group propane/butane,
wherein the weight fraction of copolymers a1) and a2) in the total weight of the cosmetic preparation is about 1.0 to about 10% by weight, and the weight ratio of cosmetic preparation a) to propellant b) is about 25:1 to about 8:1.

A first group of particularly preferred cosmetic agents contemplated herein contains, based on its total weight, about 80 to about 96% by weight of cosmetic preparation a) and about 4 to about 20% by weight of propellant, preferably about 87.5 to about 96% by weight of cosmetic preparation a) and about 4 to about 12.5% by weight of propellant b), and in particular about 92 to about 96% by weight of cosmetic preparation a) and about 4 to about 8% by weight of propellant. Preferred propellants are propane/butane mixtures. Corresponding agents are suitable in particular for use as a mousse or foam:

TABLE 1

| | Propellant [% by weight] | | | |
|---|---|---|---|---|
| Formula 1 | 4 to 20 | 4 to 20 P/B* | 4 to 12.5 P/B* | 4 to 8 P/B* |
| Formula 2 | 4 to 20 | 4 to 20 P/B* | 4 to 12.5 P/B* | 4 to 8 P/B* |
| Formula 3 | 4 to 20 | 4 to 20 P/B* | 4 to 12.5 P/B* | 4 to 8 P/B* |
| Formula 4 | 4 to 20 | 4 to 20 P/B* | 4 to 12.5 P/B* | 4 to 8 P/B* |
| Formula 5 | 4 to 20 | 4 to 20 P/B* | 4 to 12.5 P/B* | 4 to 8 P/B* |
| Formula 6 | 4 to 20 | 4 to 20 P/B* | 4 to 12.5 P/B* | 4 to 8 P/B* |
| Formula 7 | 4 to 20 | 4 to 20 P/B* | 4 to 12.5 P/B* | 4 to 8 P/B* |
| Formula 8 | 4 to 20 | 4 to 20 P/B* | 4 to 12.5 P/B* | 4 to 8 P/B* |

TABLE 1-continued

| | Propellant [% by weight] | | | |
|---|---|---|---|---|
| Formula 9 | 4 to 20 | 4 to 20 P/B* | 4 to 12.5 P/B* | 4 to 8 P/B* |
| Formula 10 | 4 to 20 | 4 to 20 P/B* | 4 to 12.5 P/B* | 4 to 8 P/B* |
| Formula 11 | 4 to 20 | 4 to 20 P/B* | 4 to 12.5 P/B* | 4 to 8 P/B* |
| Formula 12 | 4 to 20 | 4 to 20 P/B* | 4 to 12.5 P/B* | 4 to 8 P/B* |
| Formula 13 | 4 to 20 | 4 to 20 P/B* | 4 to 12.5 P/B* | 4 to 8 P/B* |
| Formula 14 | 4 to 20 | 4 to 20 P/B* | 4 to 12.5 P/B* | 4 to 8 P/B* |
| Formula 15 | 4 to 20 | 4 to 20 P/B* | 4 to 12.5 P/B* | 4 to 8 P/B* |
| Formula 16 | 4 to 20 | 4 to 20 P/B* | 4 to 12.5 P/B* | 4 to 8 P/B* |
| Formula 17 | 4 to 20 | 4 to 20 P/B* | 4 to 12.5 P/B* | 4 to 8 P/B* |
| Formula 18 | 4 to 20 | 4 to 20 P/B* | 4 to 12.5 P/B* | 4 to 8 P/B* |
| Formula 19 | 4 to 20 | 4 to 20 P/B* | 4 to 12.5 P/B* | 4 to 8 P/B* |
| Formula 20 | 4 to 20 | 4 to 20 P/B* | 4 to 12.5 P/B* | 4 to 8 P/B* |
| Formula 21 | 4 to 20 | 4 to 20 P/B* | 4 to 12.5 P/B* | 4 to 8 P/B* |
| Formula 22 | 4 to 20 | 4 to 20 P/B* | 4 to 12.5 P/B* | 4 to 8 P/B* |
| Formula 23 | 4 to 20 | 4 to 20 P/B* | 4 to 12.5 P/B* | 4 to 8 P/B* |
| Formula 24 | 4 to 20 | 4 to 20 P/B* | 4 to 12.5 P/B* | 4 to 8 P/B* |
| Formula 25 | 4 to 20 | 4 to 20 P/B* | 4 to 12.5 P/B* | 4 to 8 P/B* |
| Formula 26 | 4 to 20 | 4 to 20 P/B* | 4 to 12.5 P/B* | 4 to 8 P/B* |
| Formula 27 | 4 to 20 | 4 to 20 P/B* | 4 to 12.5 P/B* | 4 to 8 P/B* |
| Formula 28 | 4 to 20 | 4 to 20 P/B* | 4 to 12.5 P/B* | 4 to 8 P/B* |
| Formula 29 | 4 to 20 | 4 to 20 P/B* | 4 to 12.5 P/B* | 4 to 8 P/B* |
| Formula 30 | 4 to 20 | 4 to 20 P/B* | 4 to 12.5 P/B* | 4 to 8 P/B* |
| Formula 31 | 4 to 20 | 4 to 20 P/B* | 4 to 12.5 P/B* | 4 to 8 P/B* |
| Formula 32 | 4 to 20 | 4 to 20 P/B* | 4 to 12.5 P/B* | 4 to 8 P/B* |
| Formula 33 | 4 to 20 | 4 to 20 P/B* | 4 to 12.5 P/B* | 4 to 8 P/B* |
| Formula 34 | 4 to 20 | 4 to 20 P/B* | 4 to 12.5 P/B* | 4 to 8 P/B* |
| Formula 35 | 4 to 20 | 4 to 20 P/B* | 4 to 12.5 P/B* | 4 to 8 P/B* |
| Formula 36 | 4 to 20 | 4 to 20 P/B* | 4 to 12.5 P/B* | 4 to 8 P/B* |
| Formula 37 | 4 to 20 | 4 to 20 P/B* | 4 to 12.5 P/B* | 4 to 8 P/B* |
| Formula 38 | 4 to 20 | 4 to 20 P/B* | 4 to 12.5 P/B* | 4 to 8 P/B* |
| Formula 39 | 4 to 20 | 4 to 20 P/B* | 4 to 12.5 P/B* | 4 to 8 P/B* |
| Formula 40 | 4 to 20 | 4 to 20 P/B* | 4 to 12.5 P/B* | 4 to 8 P/B* |
| Formula 41 | 4 to 20 | 4 to 20 P/B* | 4 to 12.5 P/B* | 4 to 8 P/B* |
| Formula 42 | 4 to 20 | 4 to 20 P/B* | 4 to 12.5 P/B* | 4 to 8 P/B* |
| Formula 43 | 4 to 20 | 4 to 20 P/B* | 4 to 12.5 P/B* | 4 to 8 P/B* |
| Formula 44 | 4 to 20 | 4 to 20 P/B* | 4 to 12.5 P/B* | 4 to 8 P/B* |
| Formula 45 | 4 to 20 | 4 to 20 P/B* | 4 to 12.5 P/B* | 4 to 8 P/B* |
| Formula 46 | 4 to 20 | 4 to 20 P/B* | 4 to 12.5 P/B* | 4 to 8 P/B* |
| Formula 47 | 4 to 20 | 4 to 20 P/B* | 4 to 12.5 P/B* | 4 to 8 P/B* |
| Formula 48 | 4 to 20 | 4 to 20 P/B* | 4 to 12.5 P/B* | 4 to 8 P/B* |
| Formula 49 | 4 to 20 | 4 to 20 P/B* | 4 to 12.5 P/B* | 4 to 8 P/B* |
| Formula 50 | 4 to 20 | 4 to 20 P/B* | 4 to 12.5 P/B* | 4 to 8 P/B* |
| Formula 51 | 4 to 20 | 4 to 20 P/B* | 4 to 12.5 P/B* | 4 to 8 P/B* |
| Formula 52 | 4 to 20 | 4 to 20 P/B* | 4 to 12.5 P/B* | 4 to 8 P/B* |
| Formula 53 | 4 to 20 | 4 to 20 P/B* | 4 to 12.5 P/B* | 4 to 8 P/B* |
| Formula 54 | 4 to 20 | 4 to 20 P/B* | 4 to 12.5 P/B* | 4 to 8 P/B* |
| Formula 55 | 4 to 20 | 4 to 20 P/B* | 4 to 12.5 P/B* | 4 to 8 P/B* |
| Formula 56 | 4 to 20 | 4 to 20 P/B* | 4 to 12.5 P/B* | 4 to 8 P/B* |
| Formula 57 | 4 to 20 | 4 to 20 P/B* | 4 to 12.5 P/B* | 4 to 8 P/B* |
| Formula 58 | 4 to 20 | 4 to 20 P/B* | 4 to 12.5 P/B* | 4 to 8 P/B* |
| Formula 59 | 4 to 20 | 4 to 20 P/B* | 4 to 12.5 P/B* | 4 to 8 P/B* |
| Formula 60 | 4 to 20 | 4 to 20 P/B* | 4 to 12.5 P/B* | 4 to 8 P/B* |
| Formula 61 | 4 to 20 | 4 to 20 P/B* | 4 to 12.5 P/B* | 4 to 8 P/B* |
| Formula 62 | 4 to 20 | 4 to 20 P/B* | 4 to 12.5 P/B* | 4 to 8 P/B* |
| Formula 63 | 4 to 20 | 4 to 20 P/B* | 4 to 12.5 P/B* | 4 to 8 P/B* |
| Formula 64 | 4 to 20 | 4 to 20 P/B* | 4 to 12.5 P/B* | 4 to 8 P/B* |
| Formula 65 | 4 to 20 | 4 to 20 P/B* | 4 to 12.5 P/B* | 4 to 8 P/B* |
| Formula 66 | 4 to 20 | 4 to 20 P/B* | 4 to 12.5 P/B* | 4 to 8 P/B* |
| Formula 67 | 4 to 20 | 4 to 20 P/B* | 4 to 12.5 P/B* | 4 to 8 P/B* |
| Formula 68 | 4 to 20 | 4 to 20 P/B* | 4 to 12.5 P/B* | 4 to 8 P/B* |
| Formula 69 | 4 to 20 | 4 to 20 P/B* | 4 to 12.5 P/B* | 4 to 8 P/B* |
| Formula 70 | 4 to 20 | 4 to 20 P/B* | 4 to 12.5 P/B* | 4 to 8 P/B* |
| Formula 71 | 4 to 20 | 4 to 20 P/B* | 4 to 12.5 P/B* | 4 to 8 P/B* |
| Formula 72 | 4 to 20 | 4 to 20 P/B* | 4 to 12.5 P/B* | 4 to 8 P/B* |
| Formula 73 | 4 to 20 | 4 to 20 P/B* | 4 to 12.5 P/B* | 4 to 8 P/B* |
| Formula 74 | 4 to 20 | 4 to 20 P/B* | 4 to 12.5 P/B* | 4 to 8 P/B* |
| Formula 75 | 4 to 20 | 4 to 20 P/B* | 4 to 12.5 P/B* | 4 to 8 P/B* |
| Formula 76 | 4 to 20 | 4 to 20 P/B* | 4 to 12.5 P/B* | 4 to 8 P/B* |
| Formula 77 | 4 to 20 | 4 to 20 P/B* | 4 to 12.5 P/B* | 4 to 8 P/B* |
| Formula 78 | 4 to 20 | 4 to 20 P/B* | 4 to 12.5 P/B* | 4 to 8 P/B* |
| Formula 79 | 4 to 20 | 4 to 20 P/B* | 4 to 12.5 P/B* | 4 to 8 P/B* |
| Formula 80 | 4 to 20 | 4 to 20 P/B* | 4 to 12.5 P/B* | 4 to 8 P/B* |
| Formula 81 | 4 to 20 | 4 to 20 P/B* | 4 to 12.5 P/B* | 4 to 8 P/B* |
| Formula 82 | 4 to 20 | 4 to 20 P/B* | 4 to 12.5 P/B* | 4 to 8 P/B* |
| Formula 83 | 4 to 20 | 4 to 20 P/B* | 4 to 12.5 P/B* | 4 to 8 P/B* |
| Formula 84 | 4 to 20 | 4 to 20 P/B* | 4 to 12.5 P/B* | 4 to 8 P/B* |
| Formula 85 | 4 to 20 | 4 to 20 P/B* | 4 to 12.5 P/B* | 4 to 8 P/B* |
| Formula 86 | 4 to 20 | 4 to 20 P/B* | 4 to 12.5 P/B* | 4 to 8 P/B* |
| Formula 87 | 4 to 20 | 4 to 20 P/B* | 4 to 12.5 P/B* | 4 to 8 P/B* |
| Formula 88 | 4 to 20 | 4 to 20 P/B* | 4 to 12.5 P/B* | 4 to 8 P/B* |
| Formula 89 | 4 to 20 | 4 to 20 P/B* | 4 to 12.5 P/B* | 4 to 8 P/B* |
| Formula 90 | 4 to 20 | 4 to 20 P/B* | 4 to 12.5 P/B* | 4 to 8 P/B* |
| Formula 91 | 4 to 20 | 4 to 20 P/B* | 4 to 12.5 P/B* | 4 to 8 P/B* |
| Formula 92 | 4 to 20 | 4 to 20 P/B* | 4 to 12.5 P/B* | 4 to 8 P/B* |
| Formula 93 | 4 to 20 | 4 to 20 P/B* | 4 to 12.5 P/B* | 4 to 8 P/B* |
| Formula 94 | 4 to 20 | 4 to 20 P/B* | 4 to 12.5 P/B* | 4 to 8 P/B* |
| Formula 95 | 4 to 20 | 4 to 20 P/B* | 4 to 12.5 P/B* | 4 to 8 P/B* |
| Formula 96 | 4 to 20 | 4 to 20 P/B* | 4 to 12.5 P/B* | 4 to 8 P/B* |
| Formula 97 | 4 to 20 | 4 to 20 P/B* | 4 to 12.5 P/B* | 4 to 8 P/B* |
| Formula 98 | 4 to 20 | 4 to 20 P/B* | 4 to 12.5 P/B* | 4 to 8 P/B* |
| Formula 99 | 4 to 20 | 4 to 20 P/B* | 4 to 12.5 P/B* | 4 to 8 P/B* |
| Formula 100 | 4 to 20 | 4 to 20 P/B* | 4 to 12.5 P/B* | 4 to 8 P/B* |

*"P/B" corresponds to a propane/butane mixture

The indication "50 to 200% by weight" in Table 2 below corresponds to the addition of propellant to cosmetic preparation a) in a quantity of about 50 to about 200% by weight of the weight of cosmetic preparation a). In other words, cosmetic preparation a) and propellant b) are present in this cosmetic agent in a weight ratio of about 100:50 to about 100:200 and about 2:1 to about 1:2, respectively.

Accordingly, in line 4, column 3 of Table 2 below, a mixture of the propellant-free cosmetic preparation a) according to formula 3 with a propane/butane mixture is described. Accordingly, the entry in line 4, column 3 describes a cosmetic agent for the temporary deformation of keratinous fibers, comprising a) a cosmetic preparation containing
        a1) about 0.5 to about 8.0% by weight of at least one copolymer composed at least of the following monomer units:
            styrene
            acrylic acid and/or methacrylic acid;
        a2) about 0.5 to about 8.0% by weight of at least one copolymer composed at least of the following monomer units:
            N-tert-butylacrylamide
            acrylic acid
            ethyl acrylate,
    b) propellant from the group of propane/butane mixtures, wherein the weight fraction of copolymers a1) and a2) in the total weight of the cosmetic preparation is about 1.0 to about 10% by weight, and the weight ratio of cosmetic preparation a) to propellant b) is about 2:1 to about 1:2.

A second group of particularly preferred cosmetic agents contemplated herein contains, based on its total weight, about 30 to about 70% by weight of cosmetic preparation a) and about 30 to about 70% by weight of propellant b). Such agents are particularly suited for use as a spray:

TABLE 2

| | Propellant [% by weight] | | | |
|---|---|---|---|---|
| Formula 1 | 50 to 200 | 50 to 200 P/B* | 50 to 200 DFE** | 50 to 200 DME*** |
| Formula 2 | 50 to 200 | 50 to 200 P/B* | 50 to 200 DFE** | 50 to 200 DME*** |
| Formula 3 | 50 to 200 | 50 to 200 P/B* | 50 to 200 DFE** | 50 to 200 DME*** |

TABLE 2-continued

| | Propellant [% by weight] | | | |
|---|---|---|---|---|
| Formula 4 | 50 to 200 | 50 to 200 P/B* | 50 to 200 DFE** | 50 to 200 DME*** |
| Formula 5 | 50 to 200 | 50 to 200 P/B* | 50 to 200 DFE** | 50 to 200 DME*** |
| Formula 6 | 50 to 200 | 50 to 200 P/B* | 50 to 200 DFE** | 50 to 200 DME*** |
| Formula 7 | 50 to 200 | 50 to 200 P/B* | 50 to 200 DFE** | 50 to 200 DME*** |
| Formula 8 | 50 to 200 | 50 to 200 P/B* | 50 to 200 DFE** | 50 to 200 DME*** |
| Formula 9 | 50 to 200 | 50 to 200 P/B* | 50 to 200 DFE** | 50 to 200 DME*** |
| Formula 10 | 50 to 200 | 50 to 200 P/B* | 50 to 200 DFE** | 50 to 200 DME*** |
| Formula 11 | 50 to 200 | 50 to 200 P/B* | 50 to 200 DFE** | 50 to 200 DME*** |
| Formula 12 | 50 to 200 | 50 to 200 P/B* | 50 to 200 DFE** | 50 to 200 DME*** |
| Formula 13 | 50 to 200 | 50 to 200 P/B* | 50 to 200 DFE** | 50 to 200 DME*** |
| Formula 14 | 50 to 200 | 50 to 200 P/B* | 50 to 200 DFE** | 50 to 200 DME*** |
| Formula 15 | 50 to 200 | 50 to 200 P/B* | 50 to 200 DFE** | 50 to 200 DME*** |
| Formula 16 | 50 to 200 | 50 to 200 P/B* | 50 to 200 DFE** | 50 to 200 DME*** |
| Formula 17 | 50 to 200 | 50 to 200 P/B* | 50 to 200 DFE** | 50 to 200 DME*** |
| Formula 18 | 50 to 200 | 50 to 200 P/B* | 50 to 200 DFE** | 50 to 200 DME*** |
| Formula 19 | 50 to 200 | 50 to 200 P/B* | 50 to 200 DFE** | 50 to 200 DME*** |
| Formula 20 | 50 to 200 | 50 to 200 P/B* | 50 to 200 DFE** | 50 to 200 DME*** |
| Formula 21 | 50 to 200 | 50 to 200 P/B* | 50 to 200 DFE** | 50 to 200 DME*** |
| Formula 22 | 50 to 200 | 50 to 200 P/B* | 50 to 200 DFE** | 50 to 200 DME*** |
| Formula 23 | 50 to 200 | 50 to 200 P/B* | 50 to 200 DFE** | 50 to 200 DME*** |
| Formula 24 | 50 to 200 | 50 to 200 P/B* | 50 to 200 DFE** | 50 to 200 DME*** |
| Formula 25 | 50 to 200 | 50 to 200 P/B* | 50 to 200 DFE** | 50 to 200 DME*** |
| Formula 26 | 50 to 200 | 50 to 200 P/B* | 50 to 200 DFE** | 50 to 200 DME*** |
| Formula 27 | 50 to 200 | 50 to 200 P/B* | 50 to 200 DFE** | 50 to 200 DME*** |
| Formula 28 | 50 to 200 | 50 to 200 P/B* | 50 to 200 DFE** | 50 to 200 DME*** |
| Formula 29 | 50 to 200 | 50 to 200 P/B* | 50 to 200 DFE** | 50 to 200 DME*** |
| Formula 30 | 50 to 200 | 50 to 200 P/B* | 50 to 200 DFE** | 50 to 200 DME*** |
| Formula 31 | 50 to 200 | 50 to 200 P/B* | 50 to 200 DFE** | 50 to 200 DME*** |
| Formula 32 | 50 to 200 | 50 to 200 P/B* | 50 to 200 DFE** | 50 to 200 DME*** |
| Formula 33 | 50 to 200 | 50 to 200 P/B* | 50 to 200 DFE** | 50 to 200 DME*** |
| Formula 34 | 50 to 200 | 50 to 200 P/B* | 50 to 200 DFE** | 50 to 200 DME*** |
| Formula 35 | 50 to 200 | 50 to 200 P/B* | 50 to 200 DFE** | 50 to 200 DME*** |
| Formula 36 | 50 to 200 | 50 to 200 P/B* | 50 to 200 DFE** | 50 to 200 DME*** |
| Formula 37 | 50 to 200 | 50 to 200 P/B* | 50 to 200 DFE** | 50 to 200 DME*** |
| Formula 38 | 50 to 200 | 50 to 200 P/B* | 50 to 200 DFE** | 50 to 200 DME*** |
| Formula 39 | 50 to 200 | 50 to 200 P/B* | 50 to 200 DFE** | 50 to 200 DME*** |
| Formula 40 | 50 to 200 | 50 to 200 P/B* | 50 to 200 DFE** | 50 to 200 DME*** |
| Formula 41 | 50 to 200 | 50 to 200 P/B* | 50 to 200 DFE** | 50 to 200 DME*** |
| Formula 42 | 50 to 200 | 50 to 200 P/B* | 50 to 200 DFE** | 50 to 200 DME*** |
| Formula 43 | 50 to 200 | 50 to 200 P/B* | 50 to 200 DFE** | 50 to 200 DME*** |
| Formula 44 | 50 to 200 | 50 to 200 P/B* | 50 to 200 DFE** | 50 to 200 DME*** |
| Formula 45 | 50 to 200 | 50 to 200 P/B* | 50 to 200 DFE** | 50 to 200 DME*** |
| Formula 46 | 50 to 200 | 50 to 200 P/B* | 50 to 200 DFE** | 50 to 200 DME*** |
| Formula 47 | 50 to 200 | 50 to 200 P/B* | 50 to 200 DFE** | 50 to 200 DME*** |
| Formula 48 | 50 to 200 | 50 to 200 P/B* | 50 to 200 DFE** | 50 to 200 DME*** |
| Formula 49 | 50 to 200 | 50 to 200 P/B* | 50 to 200 DFE** | 50 to 200 DME*** |
| Formula 50 | 50 to 200 | 50 to 200 P/B* | 50 to 200 DFE** | 50 to 200 DME*** |
| Formula 51 | 50 to 200 | 50 to 200 P/B* | 50 to 200 DFE** | 50 to 200 DME*** |
| Formula 52 | 50 to 200 | 50 to 200 P/B* | 50 to 200 DFE** | 50 to 200 DME*** |
| Formula 53 | 50 to 200 | 50 to 200 P/B* | 50 to 200 DFE** | 50 to 200 DME*** |
| Formula 54 | 50 to 200 | 50 to 200 P/B* | 50 to 200 DFE** | 50 to 200 DME*** |
| Formula 55 | 50 to 200 | 50 to 200 P/B* | 50 to 200 DFE** | 50 to 200 DME*** |
| Formula 56 | 50 to 200 | 50 to 200 P/B* | 50 to 200 DFE** | 50 to 200 DME*** |
| Formula 57 | 50 to 200 | 50 to 200 P/B* | 50 to 200 DFE** | 50 to 200 DME*** |
| Formula 58 | 50 to 200 | 50 to 200 P/B* | 50 to 200 DFE** | 50 to 200 DME*** |
| Formula 59 | 50 to 200 | 50 to 200 P/B* | 50 to 200 DFE** | 50 to 200 DME*** |
| Formula 60 | 50 to 200 | 50 to 200 P/B* | 50 to 200 DFE** | 50 to 200 DME*** |
| Formula 61 | 50 to 200 | 50 to 200 P/B* | 50 to 200 DFE** | 50 to 200 DME*** |
| Formula 62 | 50 to 200 | 50 to 200 P/B* | 50 to 200 DFE** | 50 to 200 DME*** |
| Formula 63 | 50 to 200 | 50 to 200 P/B* | 50 to 200 DFE** | 50 to 200 DME*** |
| Formula 64 | 50 to 200 | 50 to 200 P/B* | 50 to 200 DFE** | 50 to 200 DME*** |
| Formula 65 | 50 to 200 | 50 to 200 P/B* | 50 to 200 DFE** | 50 to 200 DME*** |
| Formula 66 | 50 to 200 | 50 to 200 P/B* | 50 to 200 DFE** | 50 to 200 DME*** |
| Formula 67 | 50 to 200 | 50 to 200 P/B* | 50 to 200 DFE** | 50 to 200 DME*** |
| Formula 68 | 50 to 200 | 50 to 200 P/B* | 50 to 200 DFE** | 50 to 200 DME*** |
| Formula 69 | 50 to 200 | 50 to 200 P/B* | 50 to 200 DFE** | 50 to 200 DME*** |
| Formula 70 | 50 to 200 | 50 to 200 P/B* | 50 to 200 DFE** | 50 to 200 DME*** |
| Formula 71 | 50 to 200 | 50 to 200 P/B* | 50 to 200 DFE** | 50 to 200 DME*** |
| Formula 72 | 50 to 200 | 50 to 200 P/B* | 50 to 200 DFE** | 50 to 200 DME*** |
| Formula 73 | 50 to 200 | 50 to 200 P/B* | 50 to 200 DFE** | 50 to 200 DME*** |
| Formula 74 | 50 to 200 | 50 to 200 P/B* | 50 to 200 DFE** | 50 to 200 DME*** |
| Formula 75 | 50 to 200 | 50 to 200 P/B* | 50 to 200 DFE** | 50 to 200 DME*** |
| Formula 76 | 50 to 200 | 50 to 200 P/B* | 50 to 200 DFE** | 50 to 200 DME*** |
| Formula 77 | 50 to 200 | 50 to 200 P/B* | 50 to 200 DFE** | 50 to 200 DME*** |
| Formula 78 | 50 to 200 | 50 to 200 P/B* | 50 to 200 DFE** | 50 to 200 DME*** |
| Formula 79 | 50 to 200 | 50 to 200 P/B* | 50 to 200 DFE** | 50 to 200 DME*** |
| Formula 80 | 50 to 200 | 50 to 200 P/B* | 50 to 200 DFE** | 50 to 200 DME*** |
| Formula 81 | 50 to 200 | 50 to 200 P/B* | 50 to 200 DFE** | 50 to 200 DME*** |

TABLE 2-continued

| | Propellant [% by weight] | | | |
|---|---|---|---|---|
| Formula 82 | 50 to 200 | 50 to 200 P/B* | 50 to 200 DFE** | 50 to 200 DME*** |
| Formula 83 | 50 to 200 | 50 to 200 P/B* | 50 to 200 DFE** | 50 to 200 DME*** |
| Formula 84 | 50 to 200 | 50 to 200 P/B* | 50 to 200 DFE** | 50 to 200 DME*** |
| Formula 85 | 50 to 200 | 50 to 200 P/B* | 50 to 200 DFE** | 50 to 200 DME*** |
| Formula 86 | 50 to 200 | 50 to 200 P/B* | 50 to 200 DFE** | 50 to 200 DME*** |
| Formula 87 | 50 to 200 | 50 to 200 P/B* | 50 to 200 DFE** | 50 to 200 DME*** |
| Formula 88 | 50 to 200 | 50 to 200 P/B* | 50 to 200 DFE** | 50 to 200 DME*** |
| Formula 89 | 50 to 200 | 50 to 200 P/B* | 50 to 200 DFE** | 50 to 200 DME*** |
| Formula 90 | 50 to 200 | 50 to 200 P/B* | 50 to 200 DFE** | 50 to 200 DME*** |
| Formula 91 | 50 to 200 | 50 to 200 P/B* | 50 to 200 DFE** | 50 to 200 DME*** |
| Formula 92 | 50 to 200 | 50 to 200 P/B* | 50 to 200 DFE** | 50 to 200 DME*** |
| Formula 93 | 50 to 200 | 50 to 200 P/B* | 50 to 200 DFE** | 50 to 200 DME*** |
| Formula 94 | 50 to 200 | 50 to 200 P/B* | 50 to 200 DFE** | 50 to 200 DME*** |
| Formula 95 | 50 to 200 | 50 to 200 P/B* | 50 to 200 DFE** | 50 to 200 DME*** |
| Formula 96 | 50 to 200 | 50 to 200 P/B* | 50 to 200 DFE** | 50 to 200 DME*** |
| Formula 97 | 50 to 200 | 50 to 200 P/B* | 50 to 200 DFE** | 50 to 200 DME*** |
| Formula 98 | 50 to 200 | 50 to 200 P/B* | 50 to 200 DFE** | 50 to 200 DME*** |
| Formula 99 | 50 to 200 | 50 to 200 P/B* | 50 to 200 DFE** | 50 to 200 DME*** |
| Formula 100 | 50 to 200 | 50 to 200 P/B* | 50 to 200 DFE** | 50 to 200 DME*** |

*"P/B" corresponds to a propane/butane mixture
**"DFE" corresponds to 1,1-difluoroethane
***"DME" corresponds to dimethyl ether Vessels made of metal (aluminum, tinplate, tin), safety or shatterproof plastic, or glass externally coated with plastic, for which pressure resistance and breaking strength, corrosion resistance, ease of filling, as well as esthetic considerations, ease of handling, printability, etc., play a role are suitable as pressurized gas containers for aerosol applications. Special interior protective lacquers ensure corrosion resistance with respect to cosmetic agent a).

If the agents contemplated herein are to be sprayed on the hair, these agents are advantageously provided with a dispensing device and a spray valve. Accordingly, the resulting cosmetic products include a cosmetic agent contemplated herein and a dispensing device having a spray valve.

In one preferred embodiment, the valve has a valve cone that is coated with a lacquer or a polymeric plastic A, and a similar flexible element with a rebound characteristic such that the valve returns to the closed position (neutral position of the valve) after the actuation is completed. Corresponding cosmetic products are preferred in which the aerosol dispensing device includes a valve which has a valve cone and/or a flexible element with a rebound characteristic, which are/is coated with a lacquer or a polymeric plastic A.

In another preferred embodiment, the valve has a flexible element with a rebound characteristic and/or a valve cone made of at least one plastic B, preferably an elastomeric plastic. Here as well, cosmetic products contemplated herein are preferred in which the valve has a flexible element with a rebound characteristic and/or a valve cone made of at least one plastic B, wherein preferred plastics B are elastomeric plastics. Particularly preferred elastomeric plastics are selected from Buna, in particular Buna N, Buna 421, Buna 1602, and Buna KA 6712, neoprene, butyl, and chlorobutyl.

In another preferred embodiment, the flexible element with a rebound characteristic may be designed as a coil spring or helical compression spring. In another preferred embodiment, the flexible element with a rebound characteristic may have a one-piece design with the valve cone and may have flexible legs.

As stated at the outset, the cosmetic agents described above are characterized by special cosmetic properties for the hair, in particular advantageous properties for temporary deformation of hair. A second subject matter of the present patent application is therefore the use of an agent contemplated herein for the temporary deformation of keratin-containing fibers, in particular human hair.

A third subject matter contemplated herein is a method for the temporary deformation of keratin-containing fibers, in particular human hair, in which the keratinous fibers are acted on by a cosmetic agent as contemplated herein and temporarily fixed in shape.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A cosmetic agent for the temporary deformation of keratinous fibers, comprising:
   a) a cosmetic preparation comprising:
      a1) at least one copolymer composed at least of the following monomer units:
         styrene
         acrylic acid and/or methacrylic acid; and
      a2) at least one copolymer composed at least of the following monomer units:
         N-tert-butylacrylamide
         acrylic acid
         ethyl acrylate,
   wherein the weight fraction of copolymers a1) and a2) in the total weight of the cosmetic preparation is about 1.0 to about 10% by weight; and
   wherein the weight ratio of copolymer a1) to copolymer a2) is about 1:1 to about 3:1.

2. The cosmetic agent according to claim 1, wherein the weight fraction of copolymers a1) and a2) in the total weight of the cosmetic preparation is about 1.5 to about 9.0% by weight, respectively.

3. The cosmetic agent according to claim 2, wherein the weight fraction of copolymers a1) and a2) in the total weight of the cosmetic preparation is about 2.0 to about 8.0% by weight, respectively.

4. The cosmetic agent according to claim 1, wherein the cosmetic preparation, based on its total weight, contains about 0.1 to about 9.9% by weight of copolymer a 1).

5. The cosmetic agent according to claim 4, wherein the cosmetic preparation, based on its total weight, contains about 0.5 to about 8.5% by weight of copolymer a 1).

6. The cosmetic agent according to claim 5, wherein the cosmetic preparation, based on its total weight, contains about 1.0 to about 7.0% by weight of copolymer a 1).

7. The cosmetic agent according to claim 1, wherein the cosmetic preparation, based on its total weight, contains about 0.1 to about 9.9% by weight of copolymer a2).

8. The cosmetic agent according to claim 7, wherein the cosmetic preparation, based on its total weight, contains about 0.5 to about 8.5% by weight of copolymer a2).

9. The cosmetic agent according to claim 8, wherein the cosmetic preparation, based on its total weight, contains about 1.0 to about 7.0% by weight of copolymer a2).

10. The cosmetic agent according to claim 1, wherein the agent also comprises:
    b) at least one propellant.

11. The cosmetic agent according to claim 1, wherein the cosmetic preparation, based on its total weight contains about 40 to about 98% by weight of polar solvent.

12. The cosmetic agent according to claim 1, wherein the cosmetic preparation further comprises a polymeric organic thickener.

13. A cosmetic product comprising:
    i) a cosmetic agent comprising:
        a) a cosmetic preparation comprising:
            a1) at least one copolymer composed at least of the following monomer units:
                styrene
                acrylic acid and/or methacrylic acid; and
            a2) at least one copolymer composed at least of the following monomer units:
                N-tert-butylacrylamide
                acrylic acid
                ethyl acrylate,
            wherein the weight fraction of copolymers a1) and a2) in the total weight of the cosmetic preparation is about 1.0 to about 10% by weight; and
            wherein the weight ratio of copolymer a1) to copolymer a2) is about 1:1 to about 3:1; and
    ii) a dispensing device having a spray valve.

14. The cosmetic agent according to claim 13, wherein the cosmetic preparation, based on its total weight, contains about 0.1 to about 9.9% by weight of copolymer a 1).

15. The cosmetic agent according to claim 13, wherein the cosmetic preparation, based on its total weight, contains about 0.1 to about 9.9% by weight of copolymer a2).

16. A method for the temporary deformation of keratin-containing fibers, in particular human hair, in which the keratinous fibers are acted on by a cosmetic agent and temporarily fixed in shape, the cosmetic agent comprising:
    a) a cosmetic preparation comprising:
        a1) at least one copolymer composed at least of the following monomer units:
            styrene
            acrylic acid and/or methacrylic acid; and
        a2) at least one copolymer composed at least of the following monomer units:
            N-tert-butylacrylamide
            acrylic acid
            ethyl acrylate,
    wherein the weight fraction of copolymers a1) and a2) in the total weight of the cosmetic preparation is about 1.0 to about 10% by weight; and
    wherein the weight ratio of copolymer a1) to copolymer a2) is about 1:1 to about 3:1.

* * * * *